United States Patent [19]

Lemonnier

[11] Patent Number: 5,340,741
[45] Date of Patent: Aug. 23, 1994

[54] DEVICE FOR TESTING THE STERILITY OF A FLUID

[75] Inventor: Jean Lemonnier, le Vesinet, France

[73] Assignee: Millipore Corporation, Bedford, Mass.

[21] Appl. No.: 15,702

[22] Filed: Feb. 9, 1993

[30] Foreign Application Priority Data

Feb. 13, 1992 [FR] France ................. 92 01605

[51] Int. Cl.⁵ .............................. C12M 1/34
[52] U.S. Cl. ......................... 435/291; 435/296; 435/298; 435/311; 422/113; 220/203; 220/208; 220/240; 220/316; 220/367
[58] Field of Search ............. 220/203, 208, 240, 306, 220/316, 367; 435/31, 291, 296, 298, 311, 806; 436/1, 2; 422/113

[56] References Cited

U.S. PATENT DOCUMENTS

| | | | |
|---|---|---|---|
| 4,036,698 | 7/1977 | Bush et al. | 195/103.5 X |
| 4,049,152 | 9/1977 | Treanor | 220/209 |
| 4,215,198 | 7/1980 | Gordon | 435/31 |
| 4,291,122 | 9/1981 | Orelski | 435/31 |
| 4,351,900 | 9/1982 | Lemonnier | 435/31 |
| 4,561,558 | 12/1985 | Richman et al. | 220/203 |
| 4,640,777 | 2/1987 | Lemonnier | 210/433.2 |
| 4,799,598 | 1/1989 | McFadyen | 215/260 |
| 4,883,641 | 11/1989 | Wicks et al. | 422/50 |
| 4,889,693 | 12/1989 | Su et al. | 422/113 |
| 4,996,027 | 2/1991 | Kanner | 422/113 |

*Primary Examiner*—Robert J. Warden
*Assistant Examiner*—Krisanne M. Thornton
*Attorney, Agent, or Firm*—Andrew T. Karnakis; Paul J. Cook; Huw R. Jones

[57] ABSTRACT

A sterility testing device includes a container made up of upper and lower plastic parts between which is welded a hydrophilic microporous membrane filter. The device also includes a removable plastic lid with vent holes. The lid is adapted to be secured to the container in two different positions such that, during in-situ incubation of a culture medium after the filtration of the sample and rinsing, the lid is deformed to allow a passageway for excess pressurized air to be removed from the interior of the container while at the same time preventing ambient air from entering the container. The device thus operates with a single membrane filter and is more economical to manufacture than prior art devices.

5 Claims, 3 Drawing Sheets

DEVICE FOR TESTING THE STERILITY OF A FLUID

BACKGROUND OF THE INVENTION

The present invention concerns a single-use device for testing the sterility of a sample of fluid, in particular fluid containing antibiotics.

Until now prior art devices used for sterility testing of fluids have consisted of a closed container incorporating at least two membrane filters, a hydrophilic membrane for sampling the fluid to be analyzed, preferably under pressure, and a hydrophobic membrane which acts as an air vent to enable the required gaseous equilibrium between the inside and the outside of the container to be reached during sterility testing operation. Examples of such devices are described in U.S. Pat. Nos. 4,036,698 and 4,640,777.

SUMMARY OF THE INVENTION

An object of the present invention is to reduce the constraints of devices of the type described in the cited U.S. patents by proposing a more economical device incorporating a single membrane filter that is easy to weld.

The device in accordance with the present invention comprises a transparent rigid plastic container including an upper part, a hydrophilic microporous filter membrane and a lower part fastened to a drainage support. The two parts of the container and the microporous membrane filter are disposed between the lower edge of the upper part and the upper edge of the lower part of the container and are welded together in a fluid-tight manner at their peripheries.

This device is characterized in a preferred embodiment such that the upper part of the container has a frustoconical section whose base delimits the filter surface area of the membrane and whose other end has a smaller diameter. A funnel-shaped part extends from the smaller diameter end of the frustoconical part to an open upper end whose diameter is greater than the smaller diameter of the other end.

The device in accordance with the invention is further characterized in that the open upper end of the container is adapted to be closed by a flexible plastic lid adapted to be deformed by the pressure inside the container during incubation. This lid is provided with at least one hole to vent excess pressure without contamination from the outside environment. The lid may preferably be fitted to the container by a system of lid fastening and sealing lips cooperating with a ring provided at the open end of the container enabling air to enter when filtering the fluid sample whose sterility is to be checked and air to exit during incubation of a liquid culture medium which has been poured in the container.

BRIEF DESCRIPTION OF THE DRAWINGS

The present invention will now be described with reference to a preferred embodiment shown in the appended drawings, in which.

DESCRIPTION OF PREFERRED EMBODIMENTS

Figure 2:
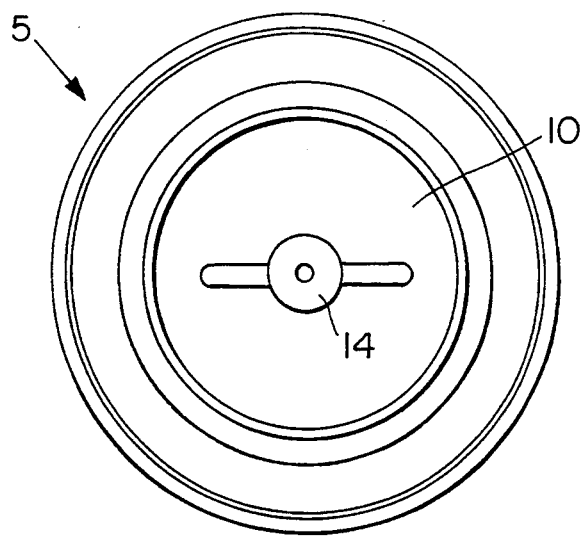
FIG. 2 is a bottom view of the device shown in FIG. 1.

The sterility testing device shown in the appended figures comprises a container 1 and a lid 2. The container consists an upper part 3, a microporous membrane filter 4 and a lower part 5. The upper part 3 has a frustoconical section 6 which has at its lower end a circular ring 13 to which the microporous membrane filter is welded and a smaller diameter in the upper end depicted by numeral 7 which forms the part of the container with the smallest diameter.

Figure 3:
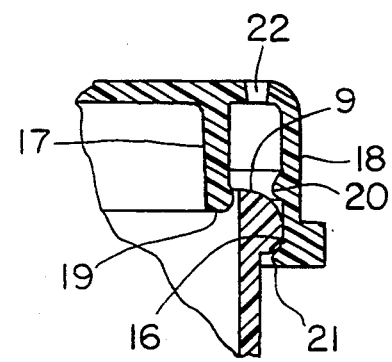
FIG. 3 is an enlarged cross-section showing the position of the lid of the device of FIG. 1 on the container during filtration of the sample.
Figure 1:
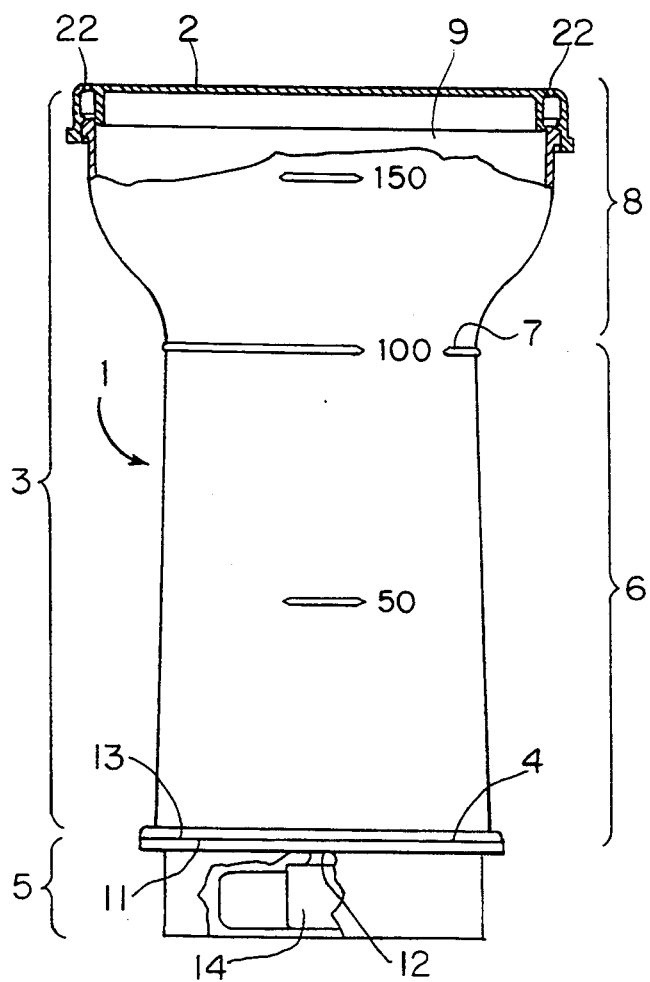
FIG. 1 is an elevation view of the device in accordance with the invention partially cut away at the bottom and partially in cross-section at the top.
Figure 4:
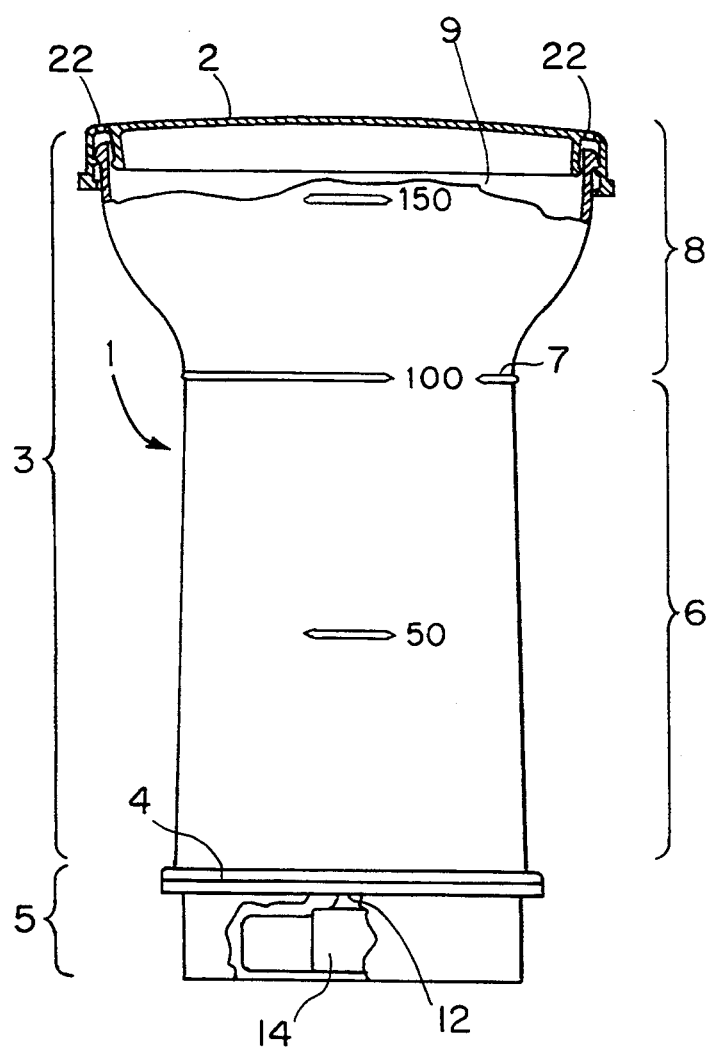
FIG. 4 is an elevation view similar to that of FIG. 1 except that the position of the lid on the container is different, being adapted for incubating a culture medium.

Referring to FIGS. 1 and 4, the frustoconical portion 6 of the upper part 3 of the container 1 is extended by a funnel-shaped section 8 widening from the smallest diameter 7 of the container towards the open upper end 9 whose diameter is greater than the smallest diameter 7. This upper end includes an outer circular ring 16 (see FIGS. 3 and 5) whose function will be explained later.

The volume of the frustoconical section 6 is chosen to be equal to the culture medium volume recommended by the various pharmacopia for incubating a culture medium. The surface of the liquid culture medium introduced into the container in accordance with the invention is located at the level of the smallest diameter 7 of the container.

The funnel shape of the section 8 of the container facilitates manual introduction of the sample to be filtered and rinsing because it is flared outwardly to a diameter which is preferably 1.5 times that of the smallest diameter 7. This shape of the section 8 also minimizes the surface area of contact with the culture medium, in particular that required to detect anaerobic microorganisms.

The lower part 5 of the container is fastened to a drainage support 10 (FIGS. 2 and 7) which includes an outer circular ring 11 and a series of concentric annular channels and radiating radial channels discharging into a central drainage orifice 12. The support 10 is also delimited by a series of fibs (not shown) which support the microporous membrane filter 4. The central drainage orifice 12 may be sealed using a small plug 14 with gripping lugs.

The hydrophilic microporous membrane filter 4 may be in the form of a continuous strip or a precut disk. Whichever form is used, the membrane filter is preferably heat welded at its periphery to the circular ring 13 of the frustoconical section 6 of the container.

Figure 6:
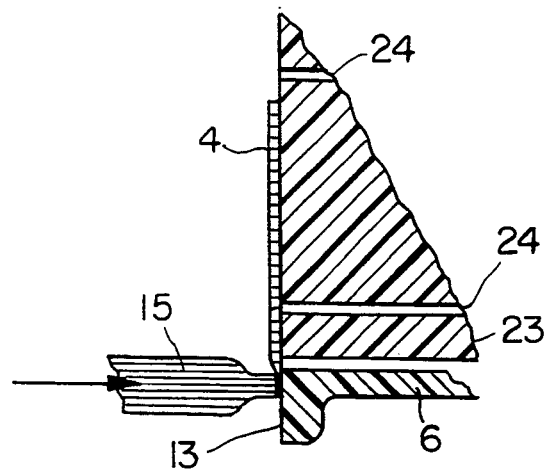
FIG. 6 is a cross-section showing the welding of the microporous membrane filter to the upper part of the container, the membrane being in the form of a disk held by a vacuum against an interior support.

In the embodiment shown in FIG. 6, the membrane filter 4 is in the form of a precut disk. The disk is held in place on a perforated support 23 inserted into the upper part 3 of the container by suction generated by creating a vacuum in the orifices 24 of the support 23. The disk-shaped membrane filter can then be welded to the lower edge of the upper part of the container using a welding tool 15. After welding, the membrane is flat and taut.

It should be noted that the use of precut disk membranes filter is not possible in the methods described in connection with the prior art devices described in the aforementioned U.S. patents since in those prior art devices the containers are entirely enclosed.

Figure 7:
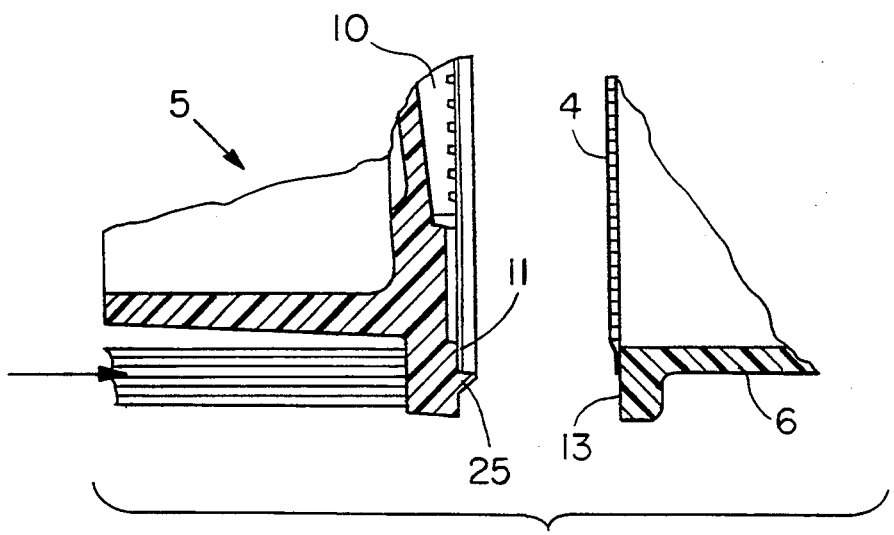
FIG. 7 is a cross-section showing the welding of the lower part of the container, fastened to a drainage support, to the upper part.
Figure 8:
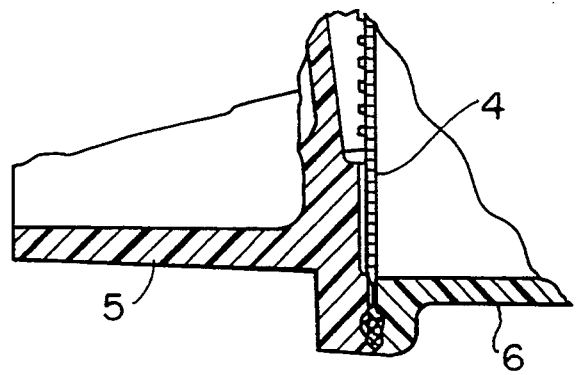
FIG. 8 is a cross-section showing the combination of the lower and upper pans of the container welded to the microporous membrane filter sandwiched between the two parts.

As shown in FIG. 7 the lower part 5 of the container fastened to the drainage support 10 has a cuneiform energy director circular bead 25 on its outer ring 11. The diameter of this bead is greater than the diameter of the membrane filter 4. The ring 13 of the upper part 3 of the container to which the membrane filter 4 has been welded is brought into contact with the ring 11 of the lower part 5 of the container. The energy director bead 25 is then heated by any appropriate means (in particular by ultrasonic means) to melt the plastic material of the container and to weld the two parts of the container together on a diameter which is greater than that of the filter membrane 4.

The use of this double weld prevents antibiotics contained in the sample placed in the upper pan of the container during filtering of the sample through the membrane filter 4 from infiltrating the weld between the two parts of the container. This is because the membrane filter is fastened to the upper part 3 and its pores have been blocked at this location during the heat welding of the membrane to the frustoconical section 6 of this part. This arrangement eliminates the risk that the growth of the microorganisms to be detected will be inhibited by antibiotic residues at the periphery of the membrane, a fact which could otherwise falsify the results of the sample sterility test.

The microporous membrane filter 4 is a polymer material preferably selected from vinylidene polyfluoride and polycarbonate and has a mean pore diameter of 0.45 μm which is sufficient to retain all microorganisms likely to be contained in the sample to be analyzed. Such retained organisms can be detected in-situ by incubation of the container after the addition of an appropriate culture medium using the techniques specified in various national pharmacopia. The plastic material from which the upper and lower parts 3 and 5 of the container 1 are made is a rigid transparent plastic material and may be selected from polystyrene, styrene or acrylonitrile resins.

The container 1 just described may be closed by a lid 2 which is made from a flexible, readily deformable plastic material such as polyethylene or an elastomer. The lid is adapted to be attached to the open upper end 9 of the container in two different positions, respectively shown in FIGS. 3 and 5.

The generally circular lid 2 comprises at its periphery two concentric axial circular skirts 17 and 18 which extend downwards. These skirts have different axial lengths, the outer skirt 18 being longer than the inner skirt 17. The inner skirt has an outside sealing lip 19 at its end and the outer skirt 18 has two inside fastening lips 20 and 21. The lip 20 faces the sealing lip 19 of the skirt 17 and the other lip 21 is located at the end of the skirt 18. The lid 2 includes two vent holes 22 each located at opposite ends of a common diameter of the lid and disposed between the two concentric skirts 17 and 18 in the annular ring defined by the two skirts.

During filtration of the fluid sample, the lid 2 is in the position shown in FIG. 3 with the open upper end 9 of the container engaged between the two skirts 17 and 18 of the lid. The outside circular ring 16 of the container is held between the two fastening lips 20 and 21 of the skirt 18. As filtration is performed under vacuum, the necessary, air can enter the container through the two vent holes 22 and the slight gap between the circular ring and the skirt 17 to maintain gaseous equilibrium between the interior of the container and the sterile ambient air.

Following filtration of the sample and rinsing, the central drainage orifice 12 is sealed by the plug 14 with gripping lugs. The culture medium is then poured into the top part of the container and the lid 2 is pressed fully down onto the outwardly flared upper part 8 of the container.

Figure 5:
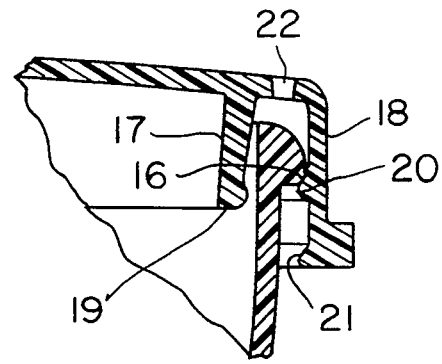
FIG. 5 is an enlarged cross-section showing the same position of the lid on the container as in FIG. 4.

Incubation of the culture medium takes place in this position, as shown in FIG. 5. The outside circular ring 16 of the container now lies between the skirts 17 and 18 having passed successively over the first fastening lip 21 and then the second fastening lip 20 of the outside skirt 18. The sealing lip 19 of the inner skirt 17 is thus in contact with the inside of the container so as to form a seal therewith.

As incubation proceeds the air inside the container is expanded as the temperature increases to the incubation temperature. This temperature rise produces a positive pressure in the container which deforms the lid 2 thereby causing the sealing lip 19 to lift away from the container to release the excess pressure. Inside air escapes through the vent holes 22 without allowing air to enter from the exterior because the second fastening lip 20 holds the lid 2 in place. Due to the maintenance of a positive pressure within the container them is no back flow of ambient air through this passageway.

The system of fining the lid to the container as described above avoids the need for an additional membrane filter covering the vent holes 22 and regulates the expulsion of excess pressure during incubation while maintaining aseptic conditions.

Although the invention has been described in terms of a preferred example, equivalents will become apparent to those of skill in the art. All such equivalents are intended to be encompassed by the accompanying claims.

I claim:

1. In a device for testing the sterility of a fluid sample of the type including a plastic container which has an upper open part, a lower part and a hydrophilic membrane filter disposed between said upper and lower parts, the upper and lower parts and the membrane filter being welded together in a fluid-tight manner at their peripheries, the improvement which comprises a deformable plastic lid, sealing means integral with said lid for closing the container from the surrounding environment, said lid including at least one vent hole and being moveable from a first position to a second position whereby when the device is filled with culture media and incubated at an elevated temperature with the lid being located in said second position said lid is constructed and arranged to be deformed by excess pressure inside the container to allow said excess pressure to escape through the vent hole while preventing the admission of ambient air through the vent hole.

2. The device of claim 1 wherein the open upper part of the container includes an exterior circular ring, said lid includes skirt means having fastening lips constructed and arranged to cooperate with said circular ring to establish two different closing positions for said lid with respect to the container.

3. The device of claim 2 wherein said skirt means comprises two concentric axial circular skirts at the periphery of the lid, the innermost skirt being provided at its edge with an exterior sealing lip constructed and arranged to cooperate with the inside wall of the open upper end of the container and the outermost skirt being provided at its edge with an interior circular fastening lip.

4. The device of claim 3 wherein the outermost circular skirt includes two circular interior fastening lips constructed and arranged to cooperate with the exterior circular ring at the upper end of the container.

5. The device of claim 3 wherein said at least one vent hole is provided in an annular ring of the lid defined by the two concentric axial skirts.

* * * * *